United States Patent
Curtin et al.

(10) Patent No.: US 6,326,194 B1
(45) Date of Patent: Dec. 4, 2001

(54) METHOD FOR PROVIDING CELL GROWTH

(76) Inventors: Geoffrey Michael Curtin, 3991-C Valley Ct.; David Wayne Bombick, 3635 High Meadows, Apt. E, both of Winston-Salem, NC (US) 27106; David James Doolittle, 2111 Hauser Rd., Lewisville, NC (US) 27023

( * ) Notice: Subject to any disclaimer, the term of this patent is extended or adjusted under 35 U.S.C. 154(b) by 0 days.

(21) Appl. No.: 08/029,855

(22) Filed: Mar. 11, 1993

(51) Int. Cl.$^7$ .................................................. C12N 5/00
(52) U.S. Cl. ...................... 435/325; 435/384; 435/391; 435/404; 435/405; 435/406
(58) Field of Search .................................. 436/70.1, 71.1; 435/240.2, 240.21, 240.22, 240.23, 240.3, 240.31, 70.1, 70.3, 325, 391, 384, 404, 405, 406

(56) References Cited

U.S. PATENT DOCUMENTS

| | | |
|---|---|---|
| 4,464,355 | 8/1984 | Fabricius et al. . |
| 5,126,261 | 6/1992 | Morris et al. . |
| 5,135,856 | 8/1992 | Tiback et al. . |
| 5,262,298 * | 11/1993 | Shipley et al. ............................ 435/6 |
| 5,316,937 * | 5/1994 | Whitehead et al. .............. 435/240.3 |

FOREIGN PATENT DOCUMENTS

| | | |
|---|---|---|
| 0403139 | 6/1990 | (EP) . |
| 9304164 * | 3/1993 | (WO) . |

OTHER PUBLICATIONS

E. W. Johnson, et al.; Serial Cultivation of Normal Human Keratinocytes: A Defined System for Studying the Regulation of Growth and Differentiation; In Vitro Cell. Dev. Biol. 28A:429–435, Jun. 1992.

R. J. Morris, et al.; Concimitant Proliferation and Formation of a Stratified Epithelial Sheet by Explant Outgrowth of Epidermal Keratinocytes from Adult Mice; In Vitro Cell. Dev. Biol. 27A:886–895, Nov., 1991.

E. Tracy Allinson, et al.; Parathyroid Hormone–Like Peptide Shares Features with Members of the Early Response Gene Family; Rapid Induction by Serum, Growth Factors, and Cycloheximide[1]; Cancer Research 52, 3103–3109, Jun. 1, 1992.

John J. Orloff, et al.; Analysis of PTHRP Binding and Signal Transduction Mechanisms in Benign and Malignant Squamous Cells: The American Physiological Society; E599–E607, 1992.

Paul W. Cook, et al.; Inhibition of Autonomous Human Keratinocyte Proliferation and Amphiregulin Mitogenic Activity by Sulfated Polysaccharides; In Vitro Cell. Dev. Biol. 28A–218–222, Mar., 1992.

Susan B. Klein, et al.; Regulation of TGF–a Expression in Human Keratinocytes: PKC–Dependent and–Independent Pathways; Journal of Cullular Physiology 154; 326–336, 1992.

K. D. Lay, et al.; UVA Modulcation of Epidermal Growth Factor Receptor Number in HELA $S_3$ Cells; Carcinogenesis vol. 13 No. 2, pp. 183–187, 1992.

Leslie L. Root, et al.; Human Dermal Fibroblasts Express Multiple bGFA and FGF Proteins; In Vitro Cell. Dev. Biol. 27A–815–822, Oct., 1991.

Michael Reiss, et al.; Activation of the Autocrine Transforming Growth Factor a Pathway in Human Squamos Carcinoma Cells[1]; Cancer Research, vol. 51, pp. 6245–6262, Dec. 1, 1991.

Nader Sceibani, et al. Malignant Human Papilomavirus Type 16–Transformed Human Keratinocytes Exhibit Altered Expression of Extracellular Matrix Glycoproteins[1]; Cancer Search 51, 5967–5975, Nov. 1, 1991.

Massimo Malcovati, et al.; Cell Density Affects Spreading and Clustering, But Not Attachment, of Human Keratinocytes in Serum–Free Medium: Journal of Cell Science 99, 387–395, 1991.

Lakshmi Khandke, Ph.D., et al.; Cyclosporine in Psoraisis Treatment; Arch Dermatol. vol. 127, pp. 1172–1179, 1991.

Francesco Minuto, et al.; Paracrine Actions of IGF Binding Proteins; Acta Endocrinologica 124: 63–69, 1991.

Mari Higashiyama, et al.; Increased Production of Transforming Factor–a in Psoriatic Epidermis; The Journal of Dermatology vol. 18, 117–119, 1991.

Simon W. Lee, et al.; Autocrine Stimulation of Interleukin–1a and Transforming Growth Factora Production in Human Keratinocytes and its Antagonism by Gluccorticoids; The Society for Investigative Dermatology, Inc.; vol. 97, No. 1, pp. 106–110, Jul., 1991.

Josephine C. Adams, et al.; Production fo Scatter Factor by NDK, a Strain of Epithelial Cells, and Inhibition of Scatter Factor Activity by Suramin; Journal of Cell–Science 98, 385–394, 1991.

Gregory Schultz, et al.; EFT and TGF–a in Wound Healing and Repair; Journal of Cellular Biochemistry 45: 346–352, 1991.

(List continued on next page.)

*Primary Examiner*—Leon B. Lankford, Jr.

(57) ABSTRACT

Growth of keratinocytes is provided by subjecting a basal medium, insulin, pituitary compound and keratinocytes to cell growth conditions. Cell growth can be provided in the absence of exogenous epidermal growth factor. A conditioned medium results after the keratinocytes are subjected to cell growth conditions, treated keratinocytes are provided, and the treated keratinocytes are subjected to cell growth conditions in a basal medium. The conditioned medium contains autocrine factor. The conditioned medium then is contacted with further keratinocytes to provide a cell growth mixture. The cell growth mixture is subjected to incubation in order to provide replicative DNA synthesis and hence cell proliferation. Cells so provided can be used for dermatological research, toxicological testing and skin grafts.

12 Claims, No Drawings

OTHER PUBLICATIONS

Eui Ju Choi, et al.; Dioxin Induces Transforming Growth Factor–a in Human Keratinocytes; The Journal of Biological Chemistry, vol. 266, No. 15, pp. 9591–9597, May 25, 1991.

Stephen Haskill, et al.; cDNA Cloning of an Intracellular Form of the Human Interleukin 1 Receptor Antagonist Associated with Epithelium; Proc. Natl. Acad. Sci. USA, vol. 88, pp. 3681–3685, May, 1991.

Paul W. Cook, et al. A Heparin Sulfate–Regulated Human Keratinocyte Autocrine Factor is Similar of Identical to Amphiregulin; Moledular and Cellular Biology, 2547–2557, May, 1991.

Glynis Scott, et al.; Localization of Basic Fibroblast Growth Factor mRNA in Melanocytic Lesions by In Situ Hybridization; The Society for Investigative Dermatology, Inc., vol. 96, No. 93, pp. 318–322, Mar., 1991.

Paul W. Cook, et al.; Growth Factor–Independent Proliferation of Normal Human Neonatal Keratinocytes: Production of Autocrine–and Paracrine Actine Mitogenic Factors; Journal of Cellular Physiology 146, pp. 277–289, 1991.

Elisabeth Nylander Ludovist, et al.; Interleukin–1 Decreases the Number of Ia$^+$ Epidermal Dendtritic Cells But Increases Their Expression of 1a Antigen; Aeta Derm Venereol (stockh) 70:391–394, 1990.

Ercem J. Atillasoy, et al.; Immunohistochemical Localization of Parathyroid Hormone–Related Protein (PTHRP) in Normal Human Skin; The Society for Investigative Dermatology, Inc.; vol. 96, No. 2, pp. 277–280, Feb., 1991.

Toru Miki, et al.; Expression cDNA Cloning of the KGF Receptor by Creation of a Transforming Autocrine Loop; Science, vol. 251, pp. 72–75, Jan., 1991.

Alec T. Harootunian, et al.; Generation of Calcium Oscillations in Fibroblasts by Positive Feedback Between Clacium and IP$_3$; Science vol. 251, p. 75, Jan., 1991.

J. N. W. N. Barker, et al.; Keratinocytes as Initiators of Inflammation; The Lancet, vol. 337, pp. 211–215, Jan. 26, 1991.

Alice B. Gottlieb; Immunologic Mechanisms in Psoriasis; The Society for Investigative Dermatology, Inc.; vol. 95, No. 5, Supplement, pp. 18S–19S, Nov., 1990.

Cathy A. Brown, et al.; Mitogenic Effects of Transforming Growth Factor Type e on Epithelial and Fibroblastic Cells—Comparison with Other Growth Factors; Experimental Cell Research 190, pp. 233–242, 1990.

Klaus Schulze–Osthoff, et al.; Expression of Basic Fibreoblast Growth Factor (bFGF) in Kaposi's Sarcoma: An Immunohistologic Study; The Society for Investigative Dermatology, Inc.; vol. 95, No. 2, pp. 238–240, Aug., 1990.

Thomas S. Kupper, M.D.; The Activated Keratinocyte: A Model for Inducible Cytokine Production by Non–Bone Marrow–Derived Cells in Cutaneous Inflammatory and Immune Repsonses; The Society for Investigative Dermatology, Inc.; vol. 94, No. 6, Supplement, pp. 146S–150S, Jun., 1990.

Adam B. Glick, et al.; Induction and Autocrine Receptor Binding of Transforming Growth Factor–B2 During Terminal Differentiation of Primary Mouse Keratinocytes; Molecular Endocrinology 50, pp. 46–52, 1990.

Fiona M. Watt, et al.; Pentapeptide Inhibitor of Epidermal Mitosis: Production and Responsiveness in Cultures of Normal, Transformed and Neoplastic Human Keratinocytes: Carcinogenesis, vol. 10, No. 12, pp. 2249–2253, 1989.

M. Partridge, et al.; Production of TGF–a and TGF–B by Cultured Keratinocytes, Skin and Oral Squamos Cell Carcinomas—Potential Autocrine Regulation of Normal and Malignant Epithelial Cell Proliferation; British Journal of Cancer, vol. 60, pp. 542–548, 1989.

Richard J. Sharpe, M.D., et al.; Cyclosporine Inhibits Basic Fibrobast Growth Factor–Driven Proliferation of Human Endothelial Cells and Keratinocytes; Arch Dermatol, vol. 125, p. 1359–1362, Oct., 1989.

Michael Reiss, M.D., et al.; Transcriptional Activation of the C–MYC Proto–Oncogene in Murine Keratinocytes Enhances the Response to Epidermal Growth Factor; The Journal of Investigative Dermatology, Inc. vol. 93, No. 1, pp. 136–141, Jul., 1989.

Yohn et al., J. Invest. Dermatol., 100(1) pp. 23–26 (1993).*

Kratz et al, J. Cell. Biochem Suppl 0 (17 Part E) p. 133 (1993).*

Kratz et al, J. Cell Biochem Suppl 0 (17 Part E) p. 132 (1993).*

Ansel et al, J. Clinical Invest., 92(2) pp. 671–678 (1993).*

*Nutritional Requirements of Cultured Cells*, edited by Katsuka, H., University Park Press, Baltimore (1978) p. 200.*

*Methods in Enzymology, vol. LVII, Cell Culture*, edited by Jakoby et al, Academic Press, N.Y. (1979) pp. 524–525 & 581–582.*

Hirobe, T., J. Exp. Zoology, 257 (2) pp. 184–194 (1991).*

Kratz et al, J. Invest. Dermatol., 97(6) pp. 1039–1043 (1991).*

* cited by examiner

METHOD FOR PROVIDING CELL GROWTH

BACKGROUND OF THE INVENTION

The present invention relates to cells and cell growth, and in particular to mammalian cells and autocrine factor.

The epithelium consists of the membranous tissue that covers the internal and free surfaces of the human body. In conjunction with associated cell systems, epithelial cells function primarily in the areas of enclosure, protection and assimilation. Among the biologically relevant human cell systems is the epidermal keratinocyte, which represents the predominant cell type within the skin epithelium.

Clonal growth of normal human keratinocytes can be achieved in a defined (e.g., serum-free) medium as described by Boyce and Ham, *J. Invest. Dermatol.*, Vol. 80, p. 33s (1983); Shipley and Pittlekow, *Arch. Dermatol*, Vol. 123, p. 1541a (1987); and in the absence of fibroblast feeder layers or extracellular matrix as described by Rheinwald and Green, *Cell*, Vol. 6, p. 331 (1975); Peehl and Hamm, *In Vitro Cell. Dev. Biol.*, Vol. 16, p. 516 (1980); Tsao et al., *J. Cell. Physiol.*, Vol. 110, p. 219 (1982). Moreover, the level of proliferative activity and the extent to which cultured keratinocytes terminally differentiate are thought to be inversely related such that the presence of exogenous medium components (e.g., epidermal growth factor), and such that a reduced concentration of extracellular calcium greatly favors cell growth. See Boyce and Hamm, *J. Invest. Dermatol.*, Vol. 81, p. 33a (1983); Wille et al., *J. Cell. Physiol.*, Vol. 121, p. 31 (1984); Pillai et al., *Cell. Physiol.*, Vol. 134, p. 229 (1988). It is also believed that keratinocyte proliferation may be influenced by an autocrine mechanism, and therefore less dependent upon the exogenous components traditionally used to supplement growth medium preparations. See, Cook et al., *J. Cell. Physiol.*, Vol. 146, p. 277 (1991) and Cook et al., *Molec. Cell Biol.*, Vol. 11(5), p. 2547 (1991).

It would be desirable to produce autocrine factor responsible for cell growth, and to provide efficient and effective methods for growing those cells which rely upon autocrine signalling.

SUMMARY OF THE INVENTION

The present invention, in one aspect, relates to a method for producing an autocrine factor. The method involves several steps. The method involves providing a cell growth medium including a basal medium, insulin and a pituitary compound. The cell growth medium can include exogenous growth factor. However, the cell growth medium does not require the presence of exogenous growth factor, can include an amount of exogenous growth factor which is lower than that traditionally employed for cell growth conditions, and can be essentially absent of exogenous growth factor. The method also involves contacting the cell growth medium with cells to provide a mixture. That mixture so provided is subjected to cell growth conditions to yield treated cells. The treated cells and medium are separated from one another, and the treated cells are retained. The treated cells are contacted with basal medium to provide a second mixture. If desired, other components used for providing cell growth (e.g., insulin, pituitary compound and/or exogenous growth factor) optionally can be incorporated in the basal medium. That second mixture is subjected to cell growth conditions to yield cells and a conditioned medium. The conditioned medium contains an autocrine factor. The cells employed most preferably are keratinocytes, and the conditioned medium most preferably contains a keratinocyte autocrine factor. As such, in a preferred aspect, keratinocyte autocrine factor can be provided in the absence of exogenous epidermal growth factor.

The present invention also relates to a method for providing replicative DNA synthesis by cells, and hence to a method for providing proliferation of cells. The method involves several steps. The method involves providing a cell growth medium. The cell growth medium is contacted with cells to provide a mixture. The mixture so provided is subjected to cell growth conditions to yield treated cells. The cell growth medium is separated from the treated cells, and the treated cells are retained. The treated cells so retained are contacted with basal medium to provide a second mixture of medium and cells. If desired, other components used for providing cell growth (e.g., insulin, pituitary compound and/or exogenous growth factor) optionally can be incorporated into the basal medium. That second mixture is subjected to cell growth conditions to provide cells and a conditioned medium. The conditioned medium is separated from the cells. The conditioned medium so provided then is employed as a cell growth medium, or a component of a cell growth medium, which is contacted with cells to provide a further mixture. The further mixture is subjected to cell growth conditions in order that the cells within the mixture experience replicative DNA synthesis, and hence experience growth. If desired, at least once during the time that the further mixture is subjected to cell growth conditions, that mixture can be contacted with (i) further conditioned medium, and/or (ii) components used for providing cell growth (e.g., basal medium, insulin, pituitary compound and/or exogenous growth factor). If desired, after cell growth conditions, the cells and medium then can be separated from one another. Preferably, the cells used to provide the conditioned medium are keratinocytes, and the cells which are grown according to the present invention are keratinocytes.

The present invention also relates to a method for providing replicative DNA synthesis by cells, and hence to a method for providing proliferation of cells. The method comprises several steps. The method involves providing a cell growth medium including basal medium, insulin and pituitary compound. The cell growth medium does not require the presence of exogenous growth factor, can include an amount of exogenous growth factor which is lower than that traditionally employed for cell growth conditions, and preferably is essentially absent of exogenous growth factor. The mixture so provided is subjected to cell growth conditions to yield a proliferation of cells. The cells and the cell growth medium can be separated from one another, and the cells can be collected. If desired, the medium so separated from the cells also can be collected and used as a component of a cell growth medium for growing a further sample of cells.

DETAILED DESCRIPTION OF THE PREFERRED EMBODIMENTS

Cells which are employed in carrying out the present invention are animal cells. Preferably, the cells are mammalian cells, and most preferably are human cells. Preferred cells are those which have the capability to produce autocrine factors. Of particular interest are the cells which make up skin.

Skin is a material which covers surfaces of the body of an animal. Skin is made up of layers of cells, which typically are characterized as an outer epidermis and an inner dermis. See, Klein-Szanto, *Skin Carcinogenesis: Mechanisms and*

*Human Relevance*, p. 45 (1989). Of particular interest is human skin. The region of skin most useful in carrying out the present invention is known as the epithelial layer. The epithelial layer is comprised predominantly of keratinocytes. It is particularly preferred to carry out the present invention using keratinocytes.

The source of skin which is used to carry out the present invention can vary. Typically, the skin used to carry out the present invention has a high keratinocyte concentration. Preferably, cells used according to the present invention are processed so as to be in a purified form having a high concentration of isolated keratinocytes. Exemplary purified skin cells have cell number purities in keratinocyte cells of greater than 90 percent, and frequently greater than 95 percent. Exemplary samples of skin cells useful in carrying out the present invention are normal human epidermal keratinocytes available from Clonetics Corp.

The basal medium which is used according to the present invention can vary. The medium is one which is capable of supporting growth of cells. Highly preferred media are serum-free. Serum-free media generally are those media which include less than about 1 percent, and usually less than about 0.1 percent serum, based on the volume of the medium. Typical basal media include those designed to have the desired types and amounts of salts, sugars, vitamins, amino acids and other relevant biochemicals in an aqueous liquid so as provide for cell growth. Exemplary media include dilute aqueous solutions having dissolved and dispersed solids contents of less than about 5 weight percent, and usually less than about 2 weight percent. Exemplary media have osmolarities sufficient such that the occurrence of osmotic stress during cell growth is avoided. Typical media have osmolarities of about 300 to about 350 mOsm. Typical media exhibit a pH at 25° C. of about 7 to about 7.5. Exemplary basal media are described in *Culture of Animal Cells: A Manual of Basic Technique*, Freshney, pp. 71–84 (1987); *Animal Cell Culture: A Practical Approach*, Freshney (edit), pp. 13–32 (1986); Ham and McKeehan, *Methods in Enzymology*: Vol. 58, pp. 44–93 (1979); and Bottenstein et al, *Methods in Enzymology*: Vol. 58, pp. 94–109 (1979). Exemplary basal media are available from Clonetics Corp., Gibco and JRH Biosciences. Such basal media are useful in carrying out preparation of the conditioned medium, and in providing for cell growth in carrying out cell proliferation.

For cell growth and for autocrine factor production, cells are contacted with the basal medium as well as other components necessary to provide for cell growth and autocrine factor production. One component is insulin. Suitable types of insulin can be obtained from a variety of sources and in a variety of ways. Insulin sources can be human, bovine, porcine, or the like, and usually insulin is derived from recombinant techniques. Suitable types of insulin are such that cell growth occurs according to the present invention in the presence of those types of insulin. Exemplary types of insulin are available from Sigma Chemical Co., Clonetics Corp. and Calbiochem Corp. Another component includes pituitary compound, which includes components of the pituitary gland. Of particular interest are components extracted from the pituitary gland. See, *Molecular Biology of the Cell*, Alberts et al, pp. 685–687 (1989). Preferred components of the pituitary gland are those components extracted from the pituitary gland. Exemplary pituitary extract is bovine pituitary extract available from Clonetics Corp.

For autocrine factor production, for replicative DNA synthesis and for cell growth, cell growth conditions are provided. Typical cell growth conditions are those that have controlled and pre-determined conditions such as temperature, relative humidity, and atmosphere; wherein cell growth medium and cells are contacted in the presence of a suitable substrate. Exemplary substrates are glass, treated polystyrene, and the like, and the selection thereof will be apparent to the skilled artisan. Such growth conditions also are referred to as incubation conditions. See, *Culture of Animal Cells: A Manual of Basic Technique*, Freshney, pp. 57–84 (1897) and *Animal Cell Culture: A Practical Approach*, Freshney (edit.), pp. 1–11 (1986) where typical cell growth conditions are described. Typically, for cell growth and autocrine factor production, the basal medium and other components of the cell growth medium are mixed together prior to addition of cells thereto, and then the resulting mixture is subjected to cell growth conditions.

The relative amounts of the components employed in carrying out the invention can vary. Typically, the amount of the particular medium which is employed is sufficient to bathe skin cells, but is not so excessive as to limit the exchange of atmospheric components with the cells during incubation. Typically, for a representative growth surface substrate having an area of 150 $cm^2$, about 30 to about 75 ml of medium is sufficient to provide growth conditions for an initial amount of about 2,500 to about 15,000 cells/$cm^2$.

For autocrine factor production and for cell growth, the medium most preferably includes basal medium as well as insulin and a pituitary compound. The relative amounts of components which make up the medium can vary. Typically, that amount of insulin ranges from about 2 to about 20, usually about 3 to about 10 ug/ml of medium. The amount of pituitary compound employed depends upon factors such as the concentration of protein present in that compound. Typically, that amount of pituitary compound ranges from about 20 to about 100, usually about 25 to about 40 ug protein/ml medium.

According to one aspect of the present invention, a cell growth medium is provided. Such a medium includes basal medium, pituitary compound and insulin. Cells are contacted with that medium, and the resulting mixture is subjected to conditions sufficient to cause cell growth and to cause some degree of cell proliferation. The degree of cell proliferation can vary, but for typical applications, the cells increase in number by a factor of at least 2, often by a factor of at least 4, and frequently by a factor of at least 8. Normally, the period of time during which the cells are subjected to cell growth conditions (i.e., the period over which the mixture is incubated) is at least about 30 minutes, often is at least about 12 hours; but usually does not exceed about 100 hours, and often does not exceed about 85 hours. After cell proliferation in the cell growth medium occurs, the medium and cells can be separated from one another (e.g., by decantation, aspiration, or other known techniques). See, Freshney, *Culture of Animal Cells: A Manual of Basic Technique*, p. 155 (1987). The resulting medium, which is referred to as a conditioned medium, can be collected. The cells which are separated from the conditioned medium also can be collected.

In another aspect of the present invention, treated cells are provided by subjecting cells to cell growth conditions in a cell growth medium (e.g., a medium which includes basal medium, insulin, pituitary compound and optional exogenous growth factor), usually for about 20 to about 36 hours. The amount of the optional exogenous growth factor which is employed can vary, and can be that amount which is traditionally used in providing for cell growth or can be a lesser amount than is traditionally used in providing for cell growth. The treated cells then are separated from the cell growth medium, and the treated cells are collected. The treated cells then are contacted with basal medium, and the resulting mixture is subjected to cell growth conditions, usually for about 24 to about 36 hours. The cells are separated from the conditioned medium which results. The conditioned medium includes an autocrine factor. An autocrine factor is produced by a type of cell and has the capability of having an affect on that type of cell.

The conditioned medium can be handled and stored in a manner similar to that which is conventional in the art. It is preferable to avoid subjecting that medium to overly hot or overly cold conditions. However, the medium can be readily handled under ambient conditions and refrigerated.

In carrying out the present invention, the medium which can be used for cell growth and which can be used for autocrine factor production includes a lesser amount of exogenous growth factor than is present in traditional processes for providing cell growth. That is, exogenous growth factor, or growth factor which is otherwise incorporated into the cell growth medium by sources other than insulin and pituitary compound, is present in an amount that is significantly lower than that traditionally employed in comparable cell growth media. Such a growth factor is a component or components that promote, sustain or allow for cell growth, particularly growth of skin cells. The exogenous growth factor is that growth factor which is incorporated into the cell growth medium prior to the time that the medium and cells therein are subjected to cell growth conditions. In preferred aspects, the cell growth medium is essentially absent of exogenous growth factor and in certain circumstances totally absent of exogenous growth factor. For example, for skin cell growth, the amount of exogenous epidermal growth factor present in the cell growth medium typically is less than about 0.5, usually is less than about 0.1, often is less than about 0.05, and frequently is less than about 0.01 ng/ml medium. For skin cell growth according to the present invention, the cell growth medium can be absent of exogenous epidermal growth factor.

According to one aspect of the present invention, cells are caused to proliferate using a conditioned medium. In one aspect, the conditioned medium is that conditioned medium which is provided by subjecting basal medium, insulin, pituitary compound and cells to incubation; however, conditioned medium which is provided using other methods (e.g., using a cell growth medium also incorporation exogenous growth factor) also can be employed. The conditioned medium also can be provided by subjecting treated cells and basal medium to incubation conditions. The conditioned medium and cells are contacted with one another, and the resulting mixture is incubated. If desired, the conditioned medium can be contacted with further medium, and that resulting mixture then is contacted with the cells and subjected to cell growth conditions. Alternatively, if desired, the conditioned medium can be contacted with the cells, and that resulting mixture then is contacted with further medium and subjected to cell growth conditions. Alternatively, if desired, the cells and further medium can be contacted, and that resulting mixture then is contacted with conditioned medium and subjected to cell growth conditions. The further medium can include basal medium, insulin, pituitary compound, exogenous growth factor, other like components, and combinations thereof. However, the process of the present invention can be carried out using only conditioned medium, and cells, without the necessity (e.g., in the absence) of any other exogenous components.

The amount of conditioned medium present in the cell growth medium can vary. For cell growth, the amount of conditioned medium employed depends upon factors such as the concentration of autocrine factor in that medium. The degree to which the conditioned medium can be diluted with basal medium can vary, and depends upon the composition of each of the conditioned medium and the basal medium. Normally, the basal medium provides components capable of sustaining cell growth, and acts as a diluent for cellularly produced toxins which at certain concentrations may interfere with cell growth. When diluted, the amount of conditioned medium relative to basal medium typically ranges from 2:1 to 1:2, usually about 1.5:1 to 1:1.5, on a volume basis.

The conditioned medium and cells then are subjected to cell growth conditions for a period of time to cause replicative DNA synthesic of cells, and preferably to produce an increased number of cells. Such a period typically is at least about 30 minutes, often at least 12 hours; but usually does not exceed about 100 hours, and often does not exceed about 85 hours. Typically, during cell growth conditions, the number of cells increases by a factor of at least 2, often by a factor of at least 4, and frequently by a factor of at least 8. After cell growth (i.e., cell proliferation) is complete, the cells and medium can be retained for further use. Alternatively, the cells and medium can be separated from one another (e.g., using decantation, aspiration, or other known techniques). The cells which are grown and are present in the medium or are collected from the conditioned medium, can be handled and isolated in an appropriate manner. See, *Culture of Animal Cells: A Manual of Basic Technique*, Freshney, p. 129 (1987).

The cells so provided have a variety of uses. For example, the skin cells so provided are useful for skin grafts, in dermatological research, for toxicological testing, and for other like applications.

The following examples are provided in order to further illustrate the invention but should not be construed as limiting the scope thereof. Unless otherwise noted, all parts and percentages are by weight.

EXAMPLE 1

Human cells were provided. The cells were keratinocytes were normal human epidermal cells derived derived from foreskins. The cells were obtained from Clonetics Corp.

Basal medium was a modified MCDB 153 medium with 0.15 mM $CaCl_2$, 0.1 mM ethanolamine, and 0.1 mM phosphorylethanolamine, and was obtained from Clonetics Corp. Bovine insulin, bovine pituitary extract (BPE), and epidermal growth factor (EGF) from human recombinant DNA were obtained from Clonetics Corp.

Cell growth or incubation conditions were provided. Such conditions involved incubating the cells in an incubator maintained at 37° C. humified (greater than 95 percent relative humidity) atmosphere of 5 percent carbon dioxide and 95 percent air.

Suspended skin cells were plated into Corning 12-well plastic tissue culture plates at a density of 10,000 cells/cm$^2$ in the following media: C-1 basal medium; C-2 basal medium with EGF at 0.1 ng/ml; C-3 basal medium with insulin at 5 ug/ml; C-4 basal medium with EGF at 0.1 ng/ml and insulin at 5 ug/ml; C-5 basal medium with BPE at 32 ug total protein/ml; C-6 basal medium with BPE at 32 ug total protein/ml and EFG at 0.1 ng/ml; Sample 1 basal medium with insulin at 5 ug/ml and BPE at 32 ug total protein/ml; and C-7 basal medium with EFG at 0.1 ng/ml, insulin at 5 ug/ml and BPE at 32 ug total protein/ml. The amount of medium used for each sample corresponds to 35 ml of medium in a tissue culture flask having a surface area of 150 cm², or 1 ml medium/4 cm² of growth surface area.

Replicative DNA synthesis, which provides an indication of cell growth, was measured as a function of $^3$H-thymidine incorporation into acid-precipitable DNA following a 1 hour pulse treatment with 10 uCi/ml (methyl-$^3$H)-thymidine. With the termination of the labeling period, cultures were washed with ice-cold buffer and solubilized with 1.0 ml of 0.1N sodium hydroxide. A 100 ul aliquot of solubilized sample was removed for determination of total protein content, and the remaining sample protein was precipitated using 5 ml of ice-cold 10 percent trichloroacetic acid. Precipitated samples were then poured over wetted Whatman 924 AH glass fiver filters held in a Millipore filtration manifold and the sample tubes rinsed with an additional 3 ml aliquot of ice-cold 10 percent trichloroacetic acid, which was also poured over the filter. Finally, filters were washed with ice-cold 95 percent ethanol, dried and assessed for radioactivity using Fisher ScintiVerse Bio-HP aqueous cocktail in a Packard Tri-Carb 2000CA liquid scintillation counter.

Cells were enumerated by the procedure described by Borenfreund et al. *Cell Biol. Toxicol.* Vol. 1, p. 55–65 (1984). Cultures were incubated in the presence of 50 ug/ml neutral red solution in treatment medium for 60 minutes at 37° C. Following this period of dye uptake, cultures were washed and fixed using a dilute (0.37 percent volume) formaldehyde solution, and the dye extracted using 0.5 ml of 1 percent acetic acid/50 percent ethanol solution. Absorbance was measured at 540 nm.

Cell growth conditions were provided for each of the samples. Cell growth was measured over time using $^3$H-thymidine incorporation and neutral red cell enumeration assays. Data are presented in Table I.

cm² with 35 ml of cell growth medium consisting of basal medium, EGF at 0.1 mg/ml, insulin at 5 µg/ml and BPE at 32 µg total protein/ml. The components of the growth medium are described in Example 1. The mixture was incubated under conditions described in Example 1 for 24 hours, during which time some cell growth occurred. The cells then were separated, by decantation, from the medium, and the cells were retained. The cells were mixed with 35 ml basal medium in the tissue culture flask and incubated under the conditions described in Example 1 for 30 hours. The cells then were separated, by decantation, from the resulting conditioned medium.

The conditioned medium which was collected was used as a cell growth medium. That is, a sample of suspended skin cells of the type described in Example 1 were plated into Corning 12-well plastic tissue culture plates at a density of 15,000 cells/cm² along with conditioned medium at 1 ml/4 cm². The resulting mixture was subjected to incubation conditions as described in Example 1. After 8 hours, replicative DNA synthesis, which is indicative of cell growth, was measured using a $^3$H-thymidine incorporation assay, yielding a result of 1023 dpm/hr/ug protein. As such, it was observed that rapid replicative DNA synthesis occurs when conditioned medium is used as a cell growth medium.

For comparison purposes, cells were similarly incubated in the described cell growth medium for 24 hours, separated from the medium and collected. The cells were mixed with basal medium and subjected to cell growth conditions. After 8 hours, replicative DNA synthesis was measured, yielding a result of 34 dpm/hr/ug protein.

What is claimed is:

1. A method for producing a conditioned medium useful for stimulating DNA synthesis in mammalian cells, comprising:
    (a) providing a cell growth medium including basal medium, insulin and a pituitary extract;

TABLE I

| | Exogenous Ingredient[1] | | | $^3$H-thymidine/Absorbance[2,3] Time (Hours)[4] | | | | |
|---|---|---|---|---|---|---|---|---|
| Sample | Insulin | BPE | EGF | 12 | 24 | 36 | 48 | 60 |
| C-1[‡] | − | − | − | 4.7/.111 | 1.9/.111 | 1.4/.104 | 1.7/.112 | 1.8/.102 |
| C-2[‡] | − | − | + | 4.8/.115 | 2.3/.108 | 2.2/.106 | 1.6/.114 | 1.6/.104 |
| C-3[‡] | + | − | − | 6.0/.180 | 6.3/.169 | 6.3/.163 | 14.9/.210 | 21.8/.196 |
| C-4[‡] | + | − | + | 9.0/.189 | 7.2/.180 | 12.3/.185 | 24.7/.208 | 30.0/.217 |
| C-5[‡] | − | + | − | 8.5/.196 | 5.6/.188 | 4.4/.178 | 14.1/.204 | 33.0/.207 |
| C-6[‡] | − | + | + | 11.8/.217 | 10.1/.195 | 9.5/.194 | 29.4/.217 | 60.1/.225 |
| C-7[‡] | + | + | + | 26.1/.212 | 54.0/.238 | 64.1/.242 | 136.1/.288 | 238.8/.342 |
| 1 | + | + | − | 14.3/.211 | 47.5/.213 | 54.5/.225 | 92.5/.279 | 199.1/.299 |

[‡]Not an example of the invention.
[1]For exogenous ingredient, "+" represents presence in growth medium of an added ingredient, and "−" represents absence in growth medium of an added ingredient.
[2]$^3$H-thymidine is reported in dpm/hr/ug protein and is determined as described in Example 1.
[3]Absorbance is determined as described in Example 1.
[4]Values of $^3$H-thymidine and Absorbance are reported at 12, 24, 36, 48 and 60 hour time intervals.

The data in Table I show that media not having certain combinations of exogenous ingredients (i.e., Sample Nos. C-1 through C-6) do not provide conditions suitable for a significant degree of cell growth. The data in Table I also show that cell proliferation occurs in a cell growth medium containing insulin, BPE and EGF (i.e., Sample No. C-7), but that cell proliferation also occurs to a significant degree in a cell growth medium containing insulin and BPE, but absent of exogenous growth factor (i.e., Sample No. 1).

EXAMPLE 2

Human cells of the type described in Example 1 were plated into a tissue culture flask having a surface area of 150

(b) culturing mammalian cells in said cell growth medium under conditions to produce a conditioned medium which stimulates DNA synthesis in cells; and
   (c) separating conditioned medium from cells and retaining the conditioned medium.

2. The method of claim 1 whereby the cells cultured in said cell growth medium are keratinocytes.

3. The method of claim 1 or 2 whereby said cell growth medium is devoid of any exogenous growth factor.

4. The method of claim 1 or 2 whereby said cell growth medium further comprises an exogenous growth factor in an amount less than about 0.1 ng/ml of growth medium.

5. The method of claim 1 or 2 whereby the cell growth medium comprises an exogenous epidermal growth factor or exogenous epidermal growth factors.

6. The method of claim 1 whereby the cell growth medium comprises an exogenous growth factor or exogenous growth factors.

7. A method for producing a conditioned medium useful for stimulating DNA synthesis in mammalian cells, comprising:

(a) providing a cell growth medium including basal medium, insulin and a pituitary extract;

(b) culturing mammalian cells with said cell growth medium;

(c) separating said cells from said cell growth medium;

(d) culturing said separated, cells in a basal medium, under conditions to produce a conditioned medium which stimulates DNA synthesis in cells; and (e) separating said cultured cell from the conditioned medium and retaining the conditioned medium.

8. The method of claim 7 whereby the cells cultured in maid cell growth medium are keratinocytes.

9. The method of claim 7 or 8 whereby said cell growth medium is devoid of any exogenous growth factor.

10. The method of claim 7 or 8 whereby said cell growth medium further comprises an exogenous growth factor in an amount less than about 0.1 ng/ml growth medium.

11. The method of claim 7 or 8 whereby the cell growth medium comprises an exogenous epidermal growth factor or exogenous epidermal growth factors.

12. The method of claim 7 whereby the cell growth medium comprises an exogenous growth factor or exogenous growth factors.

* * * * *